United States Patent
Hyman et al.

[11] Patent Number: 6,113,542
[45] Date of Patent: Sep. 5, 2000

[54] DIAGNOSTIC APPARATUS AND METHOD TO PROVIDE EFFECTIVE INTRAOCULAR PRESSURE BASED ON MEASURED THICKNESS OF THE CORNEA

[76] Inventors: George F. Hyman, 2460 Flatbush Ave., Brooklyn, N.Y. 11234; Sajjad Akhtar, 166-16 17th Ave., Whitestone, N.Y. 11357

[21] Appl. No.: 09/211,914
[22] Filed: Dec. 15, 1998
[51] Int. Cl.⁷ ...................................... A61B 3/16
[52] U.S. Cl. ...................... 600/398; 600/405; 600/561
[58] Field of Search ................................ 600/398, 405, 600/561

[56] References Cited

U.S. PATENT DOCUMENTS

| | | | |
|---|---|---|---|
| 3,690,158 | 9/1972 | Lichtenstein et al. | 73/80 |
| 3,832,891 | 9/1974 | Stuckey | 73/80 |
| 4,159,019 | 6/1979 | de Farias | 128/645 |
| 4,617,299 | 10/1986 | Knepper | 514/178 |
| 4,621,644 | 11/1986 | Eilers | 128/652 |
| 4,624,235 | 11/1986 | Krabacher et al. | 128/652 |
| 4,747,296 | 5/1988 | Feldon et al. | 73/4 |
| 4,812,448 | 3/1989 | Knepper | 514/178 |
| 4,817,432 | 4/1989 | Wallace et al. | 73/602 |
| 4,930,507 | 6/1990 | Krasnicki et al. | 128/649 |
| 4,945,913 | 8/1990 | Krasnicki et al. | 128/647 |
| 4,987,899 | 1/1991 | Brown | 128/645 |
| 5,009,892 | 4/1991 | McKinzie | 424/422 |
| 5,098,426 | 3/1992 | Sklar et al. | 606/5 |
| 5,165,415 | 11/1992 | Wallace et al. | 128/661.06 |
| 5,229,127 | 7/1993 | McInzie | 424/427 |
| 5,355,884 | 10/1994 | Bennett | 128/645 |
| 5,359,373 | 10/1994 | Koester et al. | 351/219 |
| 5,474,066 | 12/1995 | Grolman | 600/398 |
| 5,512,966 | 4/1996 | Snook | 351/205 |

*Primary Examiner*—Cary O'Connor
*Assistant Examiner*—Pamela Wingood
*Attorney, Agent, or Firm*—Cobrin & Gittes

[57] ABSTRACT

A method of and apparatus for determining intraocular pressure, automatically corrected for variations in corneal thickness. The apparatus includes an ophthalmic pachymeter having a pachymetric probe, an applanation tonometer having an applanation probe and a microprocessor. As the applanation probe touches the cornea, the ophthalmic pachymeter generates a pachymetric signal indicative of central corneal thickness. This signal is sent to and recorded by the microprocessor. When applanation occurs, the applanation tonometer generates an applanation signal indicative of intraocular pressure. This signal is sent, as well, to the microprocessor. The microprocessor, which has been programmed with an algorithm to correct the applanation signal based on the pachymetric signal, indicates the corrected value for intraocular pressure.

3 Claims, 1 Drawing Sheet

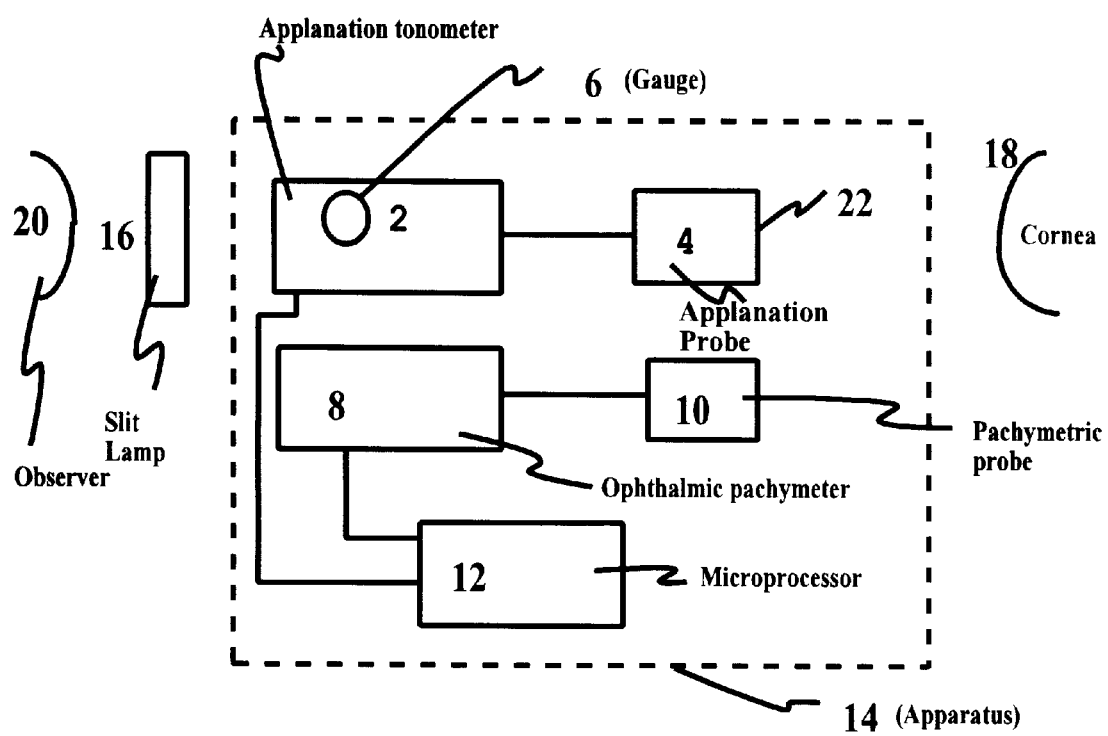

DIAGNOSTIC APPARATUS AND METHOD TO PROVIDE EFFECTIVE INTRAOCULAR PRESSURE BASED ON MEASURED THICKNESS OF THE CORNEA

BACKGROUND OF THE INVENTION

This invention relates to a method of and apparatus for determining intraocular pressure, automatically corrected for variations in corneal thickness.

Accurately calculating intraocular pressure (IOP) is important for determining the existence of disorders of the eye, such as glaucoma, which is a leading cause of blindness throughout the world. The normal human eye has an IOP of 12–19 mmHg. A high IOP is associated with glaucoma. All of the treatments available for glaucoma at present use normalization of IOP as the goal of treatment.

Accurate measurement of IOP involves cannulation of the eye. This invasive method cannot be used in general clinical practice; thus, a number of indirect methods for estimating IOP have been devised.

Applanation tonometry is the widely used method for indirect measurement of IOP. Applanation tonometry involves application of pressure at the front of the cornea of the eye, with the pressure necessary to flatten, or applanate, the surface of the cornea then used to calculate IOP. The Goldman applanation tonometer is widely used to measure IOP by this method, and has been a standard instrument for ophthamological measurement of IOP for many years.

In the calibration of his tonometer, Goldman assumed a central corneal thickness of 0.540 mm. Although he knew theoretically that central corneal thickness would influence his readings, the equipment to measure central corneal thickness accurately was not available at that time. Moreover, the fact that the human cornea has a wide range of values for central corneal thickness was not known. It is now known that human central corneal thickness can vary from 0.414 to 0.710 mm, and that race and gender may affect central corneal thickness.

In addition, new surgical techniques to correct myopia, such as photorefractive keratotomy (PRK) and laser in situ keratomileusis (LASIK) rely on resurfacing the cornea by ablating corneal tissue. Patients undergoing this increasingly popular surgery are left with thinner corneas. Although such patients are comparatively younger, over the next few decades, as they age, interpretation of IOP readings with surgically thinned corneas using Goldman's method will be misleading.

It is also now known that with Goldman applanation tonometry, the accurate reading is obtained at a mean corneal thickness of 0.545 mm. It has been shown that for every 0.070 mm variation in central corneal thickness, IOP is over- or underestimated by 5 mmHg. As a result, through the use of Goldman's method, many pressure readings in glaucoma patients may be overestimated, and many patients with genuinely high IOP may be missed. As more data become available, an increasing number of ophthalmologists are questioning the validity of readings obtained through use of the Goldman applanation tonometer.

Recently, algorithms have been developed, using both animal and human subjects, which are able to predict mmHg change in IOP with change in central corneal thickness. If both the central corneal thickness and the applanation reading are known, the effect of corneal thickness on IOP can be negated through use of these algorithms.

The use of applanation tonometry to estimate IOP is well-known in the art, and has been described, for example, in U.S. Pat. No. 5,355,884 to Bennett, and in U.S. Pat. No. 4,987,899 to Brown. Additionally, the use of ophthalmic pachymetry to calculate central corneal thickness is well-known in the art, and has been described, for example, in U.S. Pat. No. 5,512,966 to Snook. However, although it is equally well-known that the accuracy of IOP calculated via applanation tonometry is dependent on central corneal thickness, until this time no one provided automatic modification of the applanation reading based on the determination of central corneal thickness, thereby giving an accurate measure of IOP.

Accordingly, the present invention provides a method for measuring intraocular pressure through applanation tonometry and ophthalmic pachymetry, where the applanation readings are modified automatically based on the pachymetric readings, and take into account variations from the mean in central corneal thickness.

Further, the present invention provides a method for accurately determining intraocular pressure through applanation tonometry and ophthalmic pachymetry at the low and high ends of values for central corneal thickness.

Also, the present invention provides an apparatus that measures both central corneal thickness and IOP, and automatically adjusts the IOP reading according to the variation of corneal thickness around the mean, through the use of available algorithms stored in a computer chip inside a microprocessor.

SUMMARY OF THE INVENTION

The apparatus of the present invention includes an applanation tonometer having an applanation probe, an ophthalmic pachymeter having a pachymetric probe, and a microprocessor. When used according to the method of the present invention, the applanation tonometer generates an applanation signal indicative of intraocular pressure. The ophthalmic pachymeter generates a pachymetric signal indicative of central corneal thickness. The microprocessor is responsive to the applanation signal and the pachymetric signal, and is programmed to modify the applanation signal based on the pachymetric signal.

BRIEF DESCRIPTION OF THE DRAWINGS

The drawing shows a schematic representation of an arrangement of the apparatus of the present invention, including an applanation tonometer, an ophthalmic pachymeter, and a microprocessor.

DETAILED DESCRIPTION OF THE INVENTION

Turning to the drawing, the apparatus 14 of the present invention is spaced from to a slit lamp 16 as in conventional applanation tonometry.

After administering fluorescein and local anesthetic into the subject's eye, the light from the slit lamp 16 is adjusted in accordance with conventional ophthalmic practice, and the applanation probe 4 is moved in a direction towards the subject's eye until it contacts the cornea 18 of the eye.

The ophthalmic pachymeter 8 has a pachymetric probe 10 that senses the central corneal thickness as the applanation probe 4 contacts the cornea. This results in the pachymeter 8 generating a pachymetric signal, which is automatically recorded by the microprocessor 12. This signal is indicative of central corneal thickness.

The operation of an ophthalmic pachymeter 8 is known in the art, and is described in U.S. Pat. No. 5,512,966 to Snook, which is incorporated herein by reference.

After the pachymetric signal is generated, the applanation probe 4 is then moved in a direction towards the subject's eye by rotating the applanation tonometer gauge 6 until the miniscal semi-circles being visualized by an observer 20 through the slit lamp 16 become approximated, suggesting flattening of the cornea 18. At this point, an area of the cornea has been applanated by the planar surface 22 of the applanation probe 4.

The operation of an applanation tonometer 2 is known in the art, and is described in U.S. Pat. No. 5,355,884 to Bennett, which is incorporated herein by reference. The applanation probe 4 senses the intraocular hydrostatic pressure, resulting in an applanation signal generated by the applanation tonometer 2 that is an initial measure of IOP.

The applanation signal is sent to the microprocessor 12 which modifies the applanation signal based on the central corneal thickness signal generated by the ophthalmic pachymeter 8. The modified applanation signal becomes an accurate reading of IOP and may be indicated to the observer 20, such as by displaying the modified applanation reading.

Algorithms are known conventionally for correcting applanation readings based on central corneal thickness, so as to arrive at an accurate determination of IOP. One such algorithm is described in Ehlers et al., "Applanation Tonometry and Central Corneal Thickness," *Acta Ophthalmologica* 53: 34–43 (1975) ("Ehlers et al."), which is incorporated herein by reference.

Ehlers et al. compared applanation readings taken at various known intraocular hydrostatic pressures with central corneal thickness and radius in rabbit and in man. Ehlers et al. discusses a linear correlation between intraocular hydrostatic pressure and applanation tonometer reading. Ehlers et al. measured applanation readings in 29 non-edematous eyes, at 10 mmHg and 30 mmHg intraocular hydrostatic pressure. The differences between intraocular pressure and applanation reading ($\Delta P$) for each eye were compared statistically with corneal thickness and corneal radius.

Ehlers et al. found a strong linear dependence between $\Delta P$ and corneal thickness at both 10 mmHg and 30 mmHg intraocular hydrostatic pressure. No correlation was found between $\Delta P$ and corneal radius, at either level of intraocular hydrostatic pressure. Based on their findings, Ehlers et al. calculated single and multiple regression equations to determine $\Delta P$ as a function of corneal thickness (single regression) or as a function of both corneal thickness and corneal radius (multiple regression). Ehlers et al. found that, from statistical evaluation of the several regressions, it is sufficient to express $\Delta P$ as a function of corneal thickness alone. Indeed, the difference between applanation reading and IOP can be expressed as:

$$\Delta P = (1-a)P - b,$$

where $\Delta P$ is the difference between IOP and applanation reading, P is the true IOP, and a and b are variables dependent on IOP.

Ehlers et al. provide a table, reproduced below at Table I, of additive corrections ($\Delta P$) for applanation tonometer readings for IOP levels from 10 mmHg to 30 mmHg, inclusive, based on corneal thickness, from 0.450 mm to 0.590 mm, inclusive. The correction is to be added to the tonometer reading to obtain IOP in mmHg. Those corrections are incorporated into and made part of the algorithm with which the microprocessor of the present invention is programmed.

TABLE I

Additive aorrection ($\Delta P$) for Goldman applanation tonometer readings

| T | Appl. | | | | |
|---|---|---|---|---|---|
| | 10 | 15 | 20 | 25 | 30 |
| 0.450 | 4.2 | 4.7 | 5.2 | 5.7 | 6.2 |
| 0.460 | 3.5 | 4.0 | 4.4 | 4.8 | 5.3 |
| 0.470 | 2.9 | 3.3 | 3.7 | 4.1 | 4.5 |
| 0.480 | 2.2 | 2.6 | 2.9 | 3.3 | 3.6 |
| 0.490 | 1.5 | 1.8 | 2.2 | 2.5 | 2.8 |
| 0.500 | 0.9 | 1.2 | 1.4 | 1.7 | 1.9 |
| 0.510 | 0.3 | 0.5 | 0.7 | 0.9 | 1.1 |
| 0.520 | −0.4 | −0.2 | 0.0 | 0.1 | 0.3 |
| 0.530 | −1.0 | −0.8 | −0.7 | −0.6 | −0.5 |
| 0.540 | −1.6 | −1.5 | −1.4 | −1.3 | −1.2 |
| 0.550 | −2.2 | −2.1 | −2.1 | −2.0 | −2.0 |
| 0.560 | −2.8 | −2.8 | −2.8 | −2.8 | −2.7 |
| 0.570 | −3.4 | −3.4 | −3.4 | −3.4 | −3.4 |
| 0.580 | −3.9 | −4.0 | −4.1 | −4.1 | −4.2 |
| 0.590 | −4.5 | −4.6 | −4.7 | −4.8 | −4.9 |

T is thickness of the cornea in mm. Appl. is tonometer applanation reading.

Thus, by determining the central corneal thickness, via the ophthalmic pachymeter 8 of the present invention, the correct value of IOP is obtained through correction of the applanation reading based on the correction dependent on central corneal thickness.

In one embodiment of the invention, the applanation tonometer is a HaagSteik Goldman digital tonometer and the ophthalmic pachymeter is a Humphrey Instruments Model 855 Ultrasonic analog pachymeter, but modified with any conventional analog-to-digital converter incorporated into the apparatus to convert the analog signal generated by the ophthalmic pachymeter to digital. In this embodiment, the microprocessor is programmed with a regression curve for calculating IOP from the applanation reading based on the ophthalmic pachymetric reading, as described in Ehlers et al.

While preferred embodiments of the present invention have been shown and described, certain modifications and alternatives to both the apparatus and method of the present invention will readily occur to those skilled in the art. Accordingly, the present disclosure is intended to include such modifications and alternatives within the scope of the appended claims.

What is claimed is:

1. A method of measuring intraocular pressure, which automatically adjusts for variations in central corneal thickness, comprising the steps of:

a. generating a pachymetric signal with an ophthalmic pachymeter that is indicative of central corneal thickness;

b. generating an unmodified applanation signal with an applanation tonometer that is indicative of intraocular pressure;

c. modifying the otherwise unmodified applanation signal based on the pachymetric signal in accordance with a functional relationship between central corneal thickness and a difference between actual intraocular hydrostatic pressure and the unmodified applanation signal, to obtain a modified measurement of intraocular pressure;

d. providing the applanation tonometer with an applanation probe having a planar surface at one end that senses intraocular hydrostatic pressure; and e. providing the ophthalmic pachymeter with a pachymetric probe that senses central corneal thickness.

2. A method as in claim 1, further comprising:

providing a microprocessor responsive to said applanation signal and said pachymetric signal, the microprocessor being programmed to carry out the step of modifying the applanation signal based on the pachymetric signal.

3. An apparatus for determining intraocular pressure, which automatically adjusts for variations in central corneal thickness, comprising:

a. an applanation tonometer, which is adapted to generate an unmodified applanation signal indicative of intraocular hydrostatic pressure, said applanation tonometer having an applanation probe with a planar surface at one end that senses intraocular hydrostatic pressure;

b. an ophthalmic pachymeter, which is adapted to generate a pachymetric signal indicative of central corneal thickness, said ophthalmic pachymeter having a pachymetric probe that senses the central corneal thickness; and c. a microprocessor responsive to said applanation signal and said pachymetric signal to modify the applanation signal based on the pachymetric signal and in accordance with a functional relationship between central corneal thickness and a difference between actual intraocular hydrostatic pressure and the unmodified applanation signal.

* * * * *